(12) United States Patent
Lantz et al.

(10) Patent No.: US 10,386,501 B2
(45) Date of Patent: Aug. 20, 2019

(54) APPARATUS FOR DETECTING ELECTROMAGNETIC RADIATION AND METHOD AND COMPUTER PROGRAM FOR CONTROLLING AN APPARATUS FOR DETECTING ELECTROMAGNETIC RADIATION

(71) Applicant: Nokia Technologies Oy, Espoo (FI)

(72) Inventors: Vuokko Lantz, Vantaa (FI); Lea Myyrylainen, Espoo (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 15/779,149

(22) PCT Filed: Dec. 9, 2016

(86) PCT No.: PCT/FI2016/050861
§ 371 (c)(1),
(2) Date: May 25, 2018

(87) PCT Pub. No.: WO2017/109276
PCT Pub. Date: Jun. 29, 2017

(65) Prior Publication Data
US 2018/0348380 A1 Dec. 6, 2018

(30) Foreign Application Priority Data
Dec. 22, 2015 (EP) .................... 15202142

(51) Int. Cl.
*G01T 1/20* (2006.01)
*A61B 6/14* (2006.01)
*A61B 6/00* (2006.01)

(52) U.S. Cl.
CPC ............ *G01T 1/2006* (2013.01); *A61B 6/145* (2013.01); *A61B 6/5205* (2013.01);
(Continued)

(58) Field of Classification Search
CPC ....... G01T 1/2018; G01T 1/20; G01T 1/2006; H01L 27/14658; A61B 6/5205; A61B 6/5294; A61B 6/145; A61B 6/5223
See application file for complete search history.

(56) References Cited

U.S. PATENT DOCUMENTS

| 5,913,825 | A | * | 6/1999 | Watanabe | ............ | A61B 8/4281 |
| | | | | | | 600/459 |
| 2003/0031296 | A1 | * | 2/2003 | Hoheisel | ............... | G01T 1/2018 |
| | | | | | | 378/98.8 |

(Continued)

FOREIGN PATENT DOCUMENTS

| DE | 101 36 756 A1 | 2/2003 |
| JP | 2005304866 A | * 11/2005 |
| WO | WO 2014/069818 A1 | 5/2014 |

*Primary Examiner* — Kiho Kim
(74) *Attorney, Agent, or Firm* — Harrington & Smith

(57) ABSTRACT

An apparatus including a detector configured to detect electromagnetic radiation where the detector includes a first portion and a second portion; a deformable substrate configured to support the detector such that the first portion of detector is moveable relative to the second portion of the detector; and a sensor configured to detect deformation of the substrate and provide information indicative of the detected deformation to image processing circuitry.

20 Claims, 6 Drawing Sheets

Figure 1:
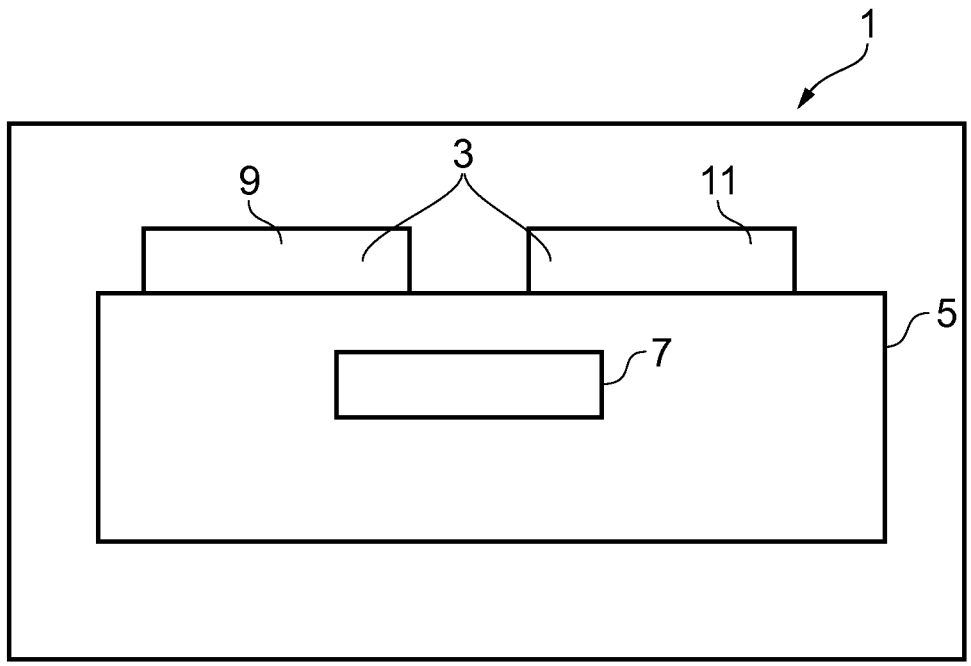

(52) U.S. Cl.
CPC .......... *A61B 6/5223* (2013.01); *A61B 6/5294* (2013.01); *G01T 1/20* (2013.01)

(56) References Cited

U.S. PATENT DOCUMENTS

| | | | |
|---|---|---|---|
| 2005/0226389 A1 | 10/2005 | Yoon et al. .................... | 378/191 |
| 2014/0284485 A1 | 9/2014 | Nagano et al. ............... | 250/366 |
| 2016/0070006 A1* | 3/2016 | Konkle .................... | G01T 1/208 |
| | | | 250/366 |
| 2016/0287198 A1* | 10/2016 | Abramovich .......... | A61B 6/105 |

* cited by examiner

APPARATUS FOR DETECTING ELECTROMAGNETIC RADIATION AND METHOD AND COMPUTER PROGRAM FOR CONTROLLING AN APPARATUS FOR DETECTING ELECTROMAGNETIC RADIATION

TECHNOLOGICAL FIELD

Examples of the disclosure relate to an apparatus for detecting electromagnetic radiation and method and computer program for controlling an apparatus for detecting electromagnetic radiation. In particular, they relate to an apparatus for detecting electromagnetic radiation and method and computer program for controlling an apparatus for detecting electromagnetic radiation using a deformable electromagnetic radiation detector.

BACKGROUND

Electromagnetic radiation such as x-ray detectors which convert incident electromagnetic radiation into an electrical output signal are known. Such detectors enable images such as x-ray images of objects to be obtained. Such detectors have a wide range of uses in medical, security and industrial applications.

It is useful to provide an apparatus which enables improved images such as x-ray images to be obtained.

BRIEF SUMMARY

According to various, but not necessarily all, examples of the disclosure there may be provided an apparatus comprising: a detector configured to detect electromagnetic radiation where the detector comprises a first portion and a second portion; a deformable substrate configured to support the detector such that the first portion of detector is moveable relative to the second portion of the detector; and a sensor configured to detect deformation of the substrate and provide information indicative of the detected deformation to image processing circuitry.

The detector for detecting electromagnetic radiation may comprise a flexible detector.

The flexible detector may comprise graphene.

The deformable substrate may comprise a flexible substrate.

The deformable substrate may comprise a plurality of hinged segments.

The plurality of hinged segments may comprise at least one segment having a first radius of curvature and at least one segment having a second radius of curvature where the first radius of curvature and the second radius of curvature are different.

The apparatus may comprise a controller configured to control the deformation of the substrate.

According to various, but not necessarily all, examples of the disclosure there may be provided an intraoral electromagnetic radiation detector comprising an apparatus as described above.

According to various, but not necessarily all, examples of the disclosure there may be provided a system comprising an apparatus as described above and at least one electromagnetic radiation source.

The system may comprise a plurality of electromagnetic radiation sources where a first electromagnetic radiation source is configured to provide electromagnetic radiation to a first portion of the electromagnetic radiation detector and a second electromagnetic radiation source is configured to provide electromagnetic radiation to the second portion of the electromagnetic radiation detector.

The system may comprise an electromagnetic radiation source configured to be moved between a first position and a second position wherein in the first position the electromagnetic radiation source is configured to provide electromagnetic radiation to a first portion of the electromagnetic radiation detector and in the second position the electromagnetic radiation source is configured to provide electromagnetic radiation to the second portion of the electromagnetic radiation detector.

The system may comprise one or more electromagnetic radiation sources provided on the deformable substrate.

According to various, but not necessarily all, examples of the disclosure there may be provided a method comprising; obtaining an image signal from a detector for detecting electromagnetic radiation where the detector comprises a first portion and a second portion and is supported on a deformable substrate such that deformation of the deformable substrate enables the first portion to be moved relative to the second portion; obtaining a deformation signal from the deformable substrate comprising information indicative of the deformation of the substrate; and using the information indicative of the deformation to process the image signal.

The image signal may comprise information obtained from a first portion of the detector and information obtained from the second portion of the detector.

The information obtained from a first portion of the detector may be obtained with first exposure settings and the information obtained from a second portion of the detector is obtained with second exposure settings where the first exposure settings and the second exposure settings are different.

The method may comprise using the information indicative of the deformation of the substrate to control at least one of the first and second exposure settings.

The method may comprise using the information from the detector to control at least one of the first and second exposure settings.

The method may comprise controlling a first electromagnetic radiation source to provide electromagnetic radiation to a first portion of the detector and controlling a second electromagnetic radiation source to provide electromagnetic radiation to a second portion of the detector.

The method may comprise controlling an electromagnetic radiation source to be moved between a first position for providing electromagnetic radiation to a first portion of the detector and a second position for providing electromagnetic radiation to a second portion of the detector.

The method may comprise processing the image signal using the deformation signal to provide a three dimensional image of an object.

The method may comprise transmitting image information to a remote device.

According to various, but not necessarily all, examples of the disclosure there may be provided an apparatus comprising: processing circuitry; and memory circuitry including computer program code, the memory circuitry and the computer program code configured to, with the processing circuitry, enable the apparatus to perform: obtaining an image signal from a detector for detecting electromagnetic radiation where the detector comprises a first portion and a second portion and is supported on a deformable substrate such that deformation of the deformable substrate enables the first portion to be moved relative to the second portion;

obtaining a deformation signal from the deformable substrate comprising information indicative of the deformation of the substrate; and using the information indicative of the deformation to process the image signal.

The image signal may comprise information obtained from a first portion of the detector and information obtained from the second portion of the detector.

The information obtained from a first portion of the detector may be obtained with first exposure settings and the information obtained from a second portion of the detector is obtained with second exposure settings where the first exposure settings and the second exposure settings are different.

The processing circuitry and memory circuitry may be configured to enable the apparatus to perform using the information indicative of the deformation of the substrate to control at least one of the first and second exposure settings.

The processing circuitry and memory circuitry may be configured to enable the apparatus to perform using the information from the detector to control at least one of the first and second exposure settings.

The processing circuitry and memory circuitry may be configured to enable the apparatus to perform controlling a first electromagnetic radiation source to provide electromagnetic radiation to a first portion of the detector and controlling a second electromagnetic radiation source to provide electromagnetic radiation to a second portion of the detector.

The processing circuitry and memory circuitry may be configured to enable the apparatus to perform controlling an electromagnetic radiation source to be moved between a first position for providing electromagnetic radiation to a first portion of the detector and a second position for providing electromagnetic radiation to a second portion of the detector.

The processing circuitry and memory circuitry may be configured to enable the apparatus to perform processing the image signal using the deformation signal to provide a three dimensional image of an object.

The processing circuitry and memory circuitry may be configured to transmit image information to a remote device.

According to various, but not necessarily all, examples of the disclosure there may be provided a system comprising an apparatus as described above and at least one remote device wherein the remote device is configured to store information obtained by the apparatus.

According to various, but not necessarily all, examples of the disclosure there may be provided a computer program comprising computer program instructions that, when executed by processing circuitry, enable: obtaining an image signal from a detector for detecting electromagnetic radiation where the detector comprises a first portion and a second portion and is supported on a deformable substrate such that deformation of the substrate enables the first portion to be moved relative to the second portion; obtaining a deformation signal from the deformable substrate comprising information indicative of the deformation of the substrate; and using the information indicative of the deformation to process the image signal.

According to various, but not necessarily all, examples of the disclosure there may be provided a computer program comprising program instructions for causing a computer to perform the method as described.

According to various, but not necessarily all, examples of the disclosure there may be provided a physical entity embodying the computer program as described above.

According to various, but not necessarily all, examples of the disclosure there may be provided an electromagnetic carrier signal carrying the computer program as claimed described above.

According to various, but not necessarily all, examples of the disclosure there is provided examples as claimed in the appended claims.

BRIEF DESCRIPTION

Figure 2:
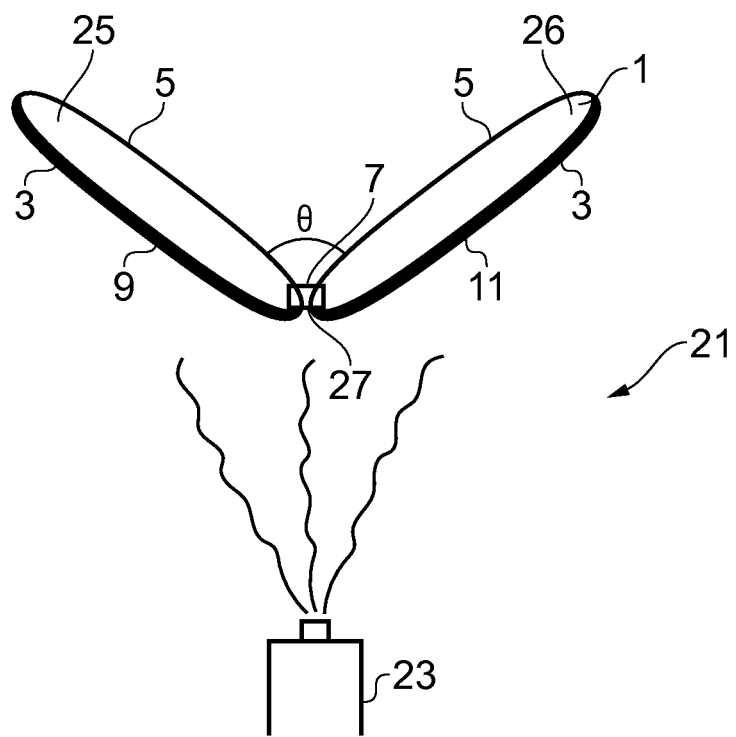
Figure 3:
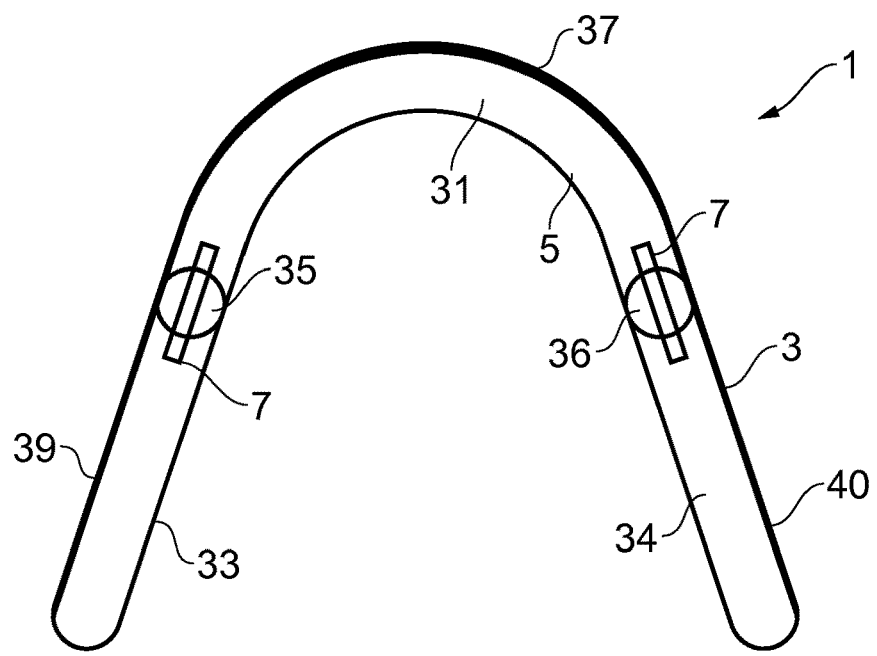
Figure 4:
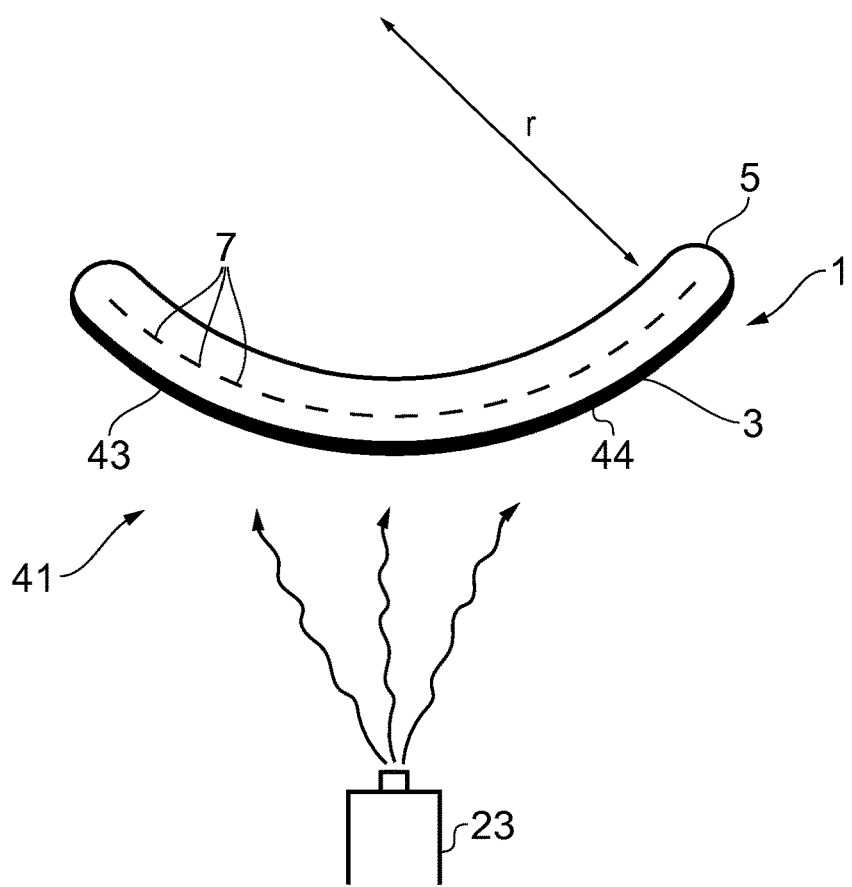
Figure 5:
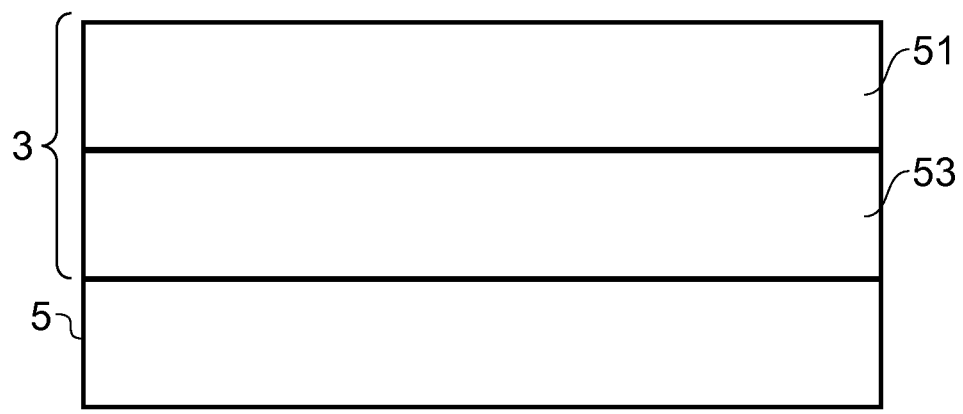
Figure 6:
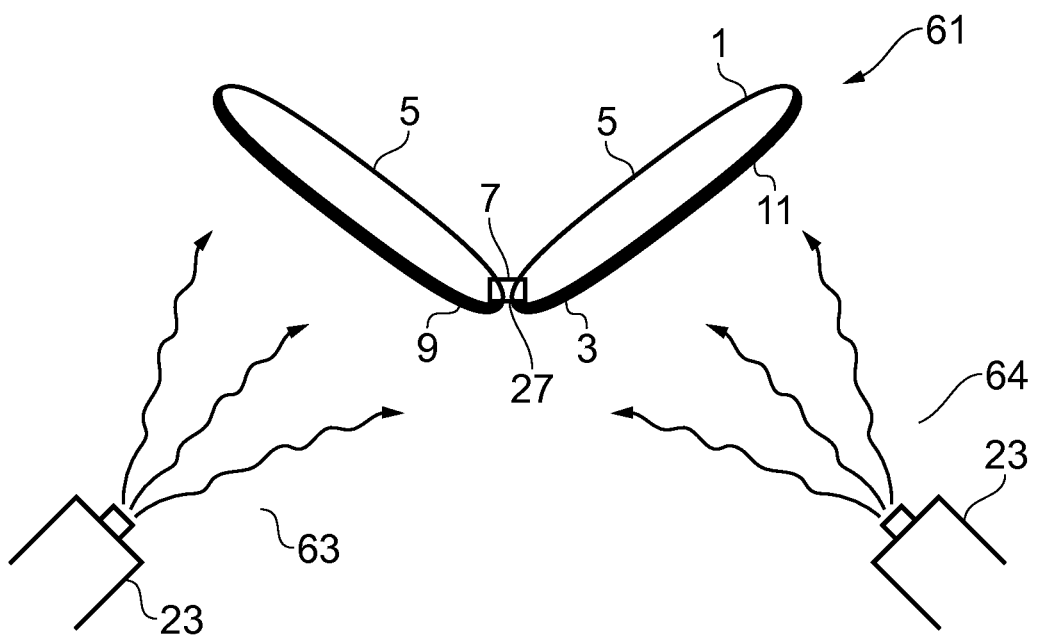
Figure 7:
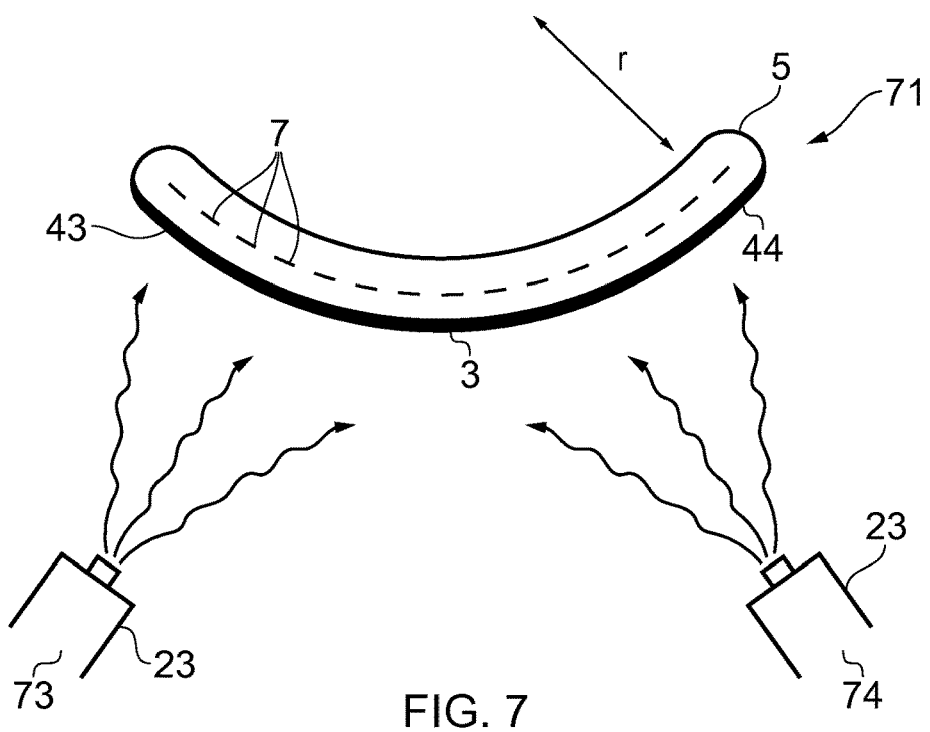
Figure 8:
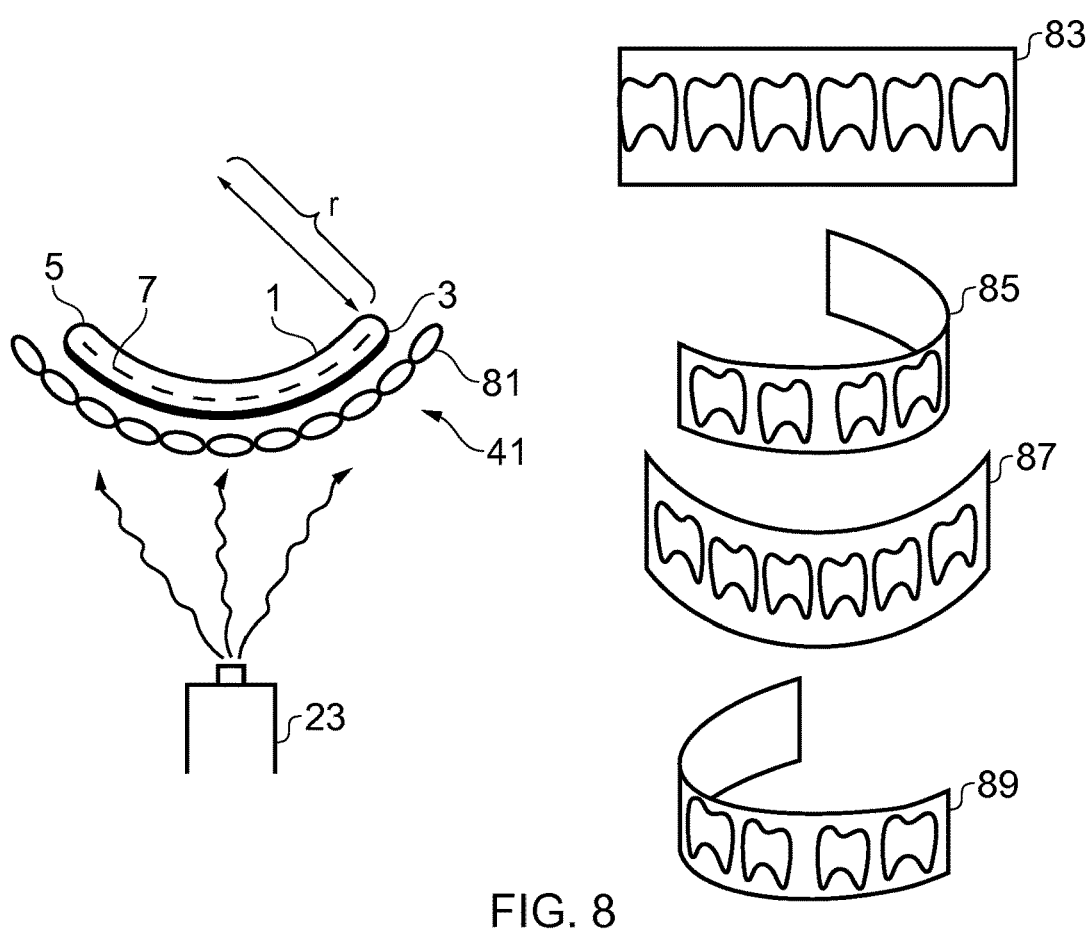
Figure 9:
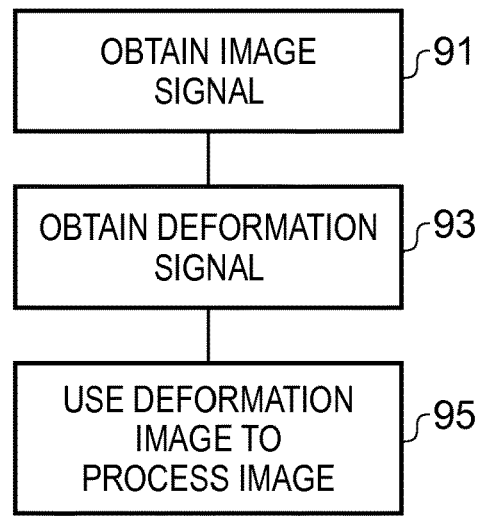
Figure 10:
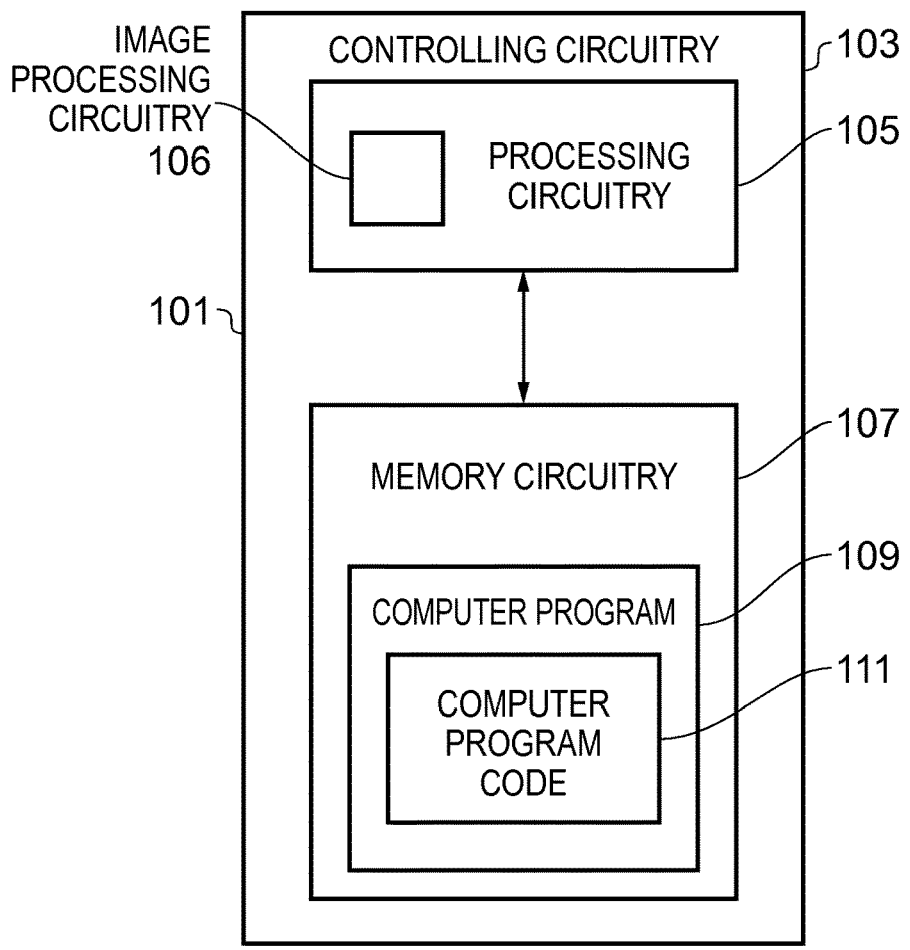
Figure 11:
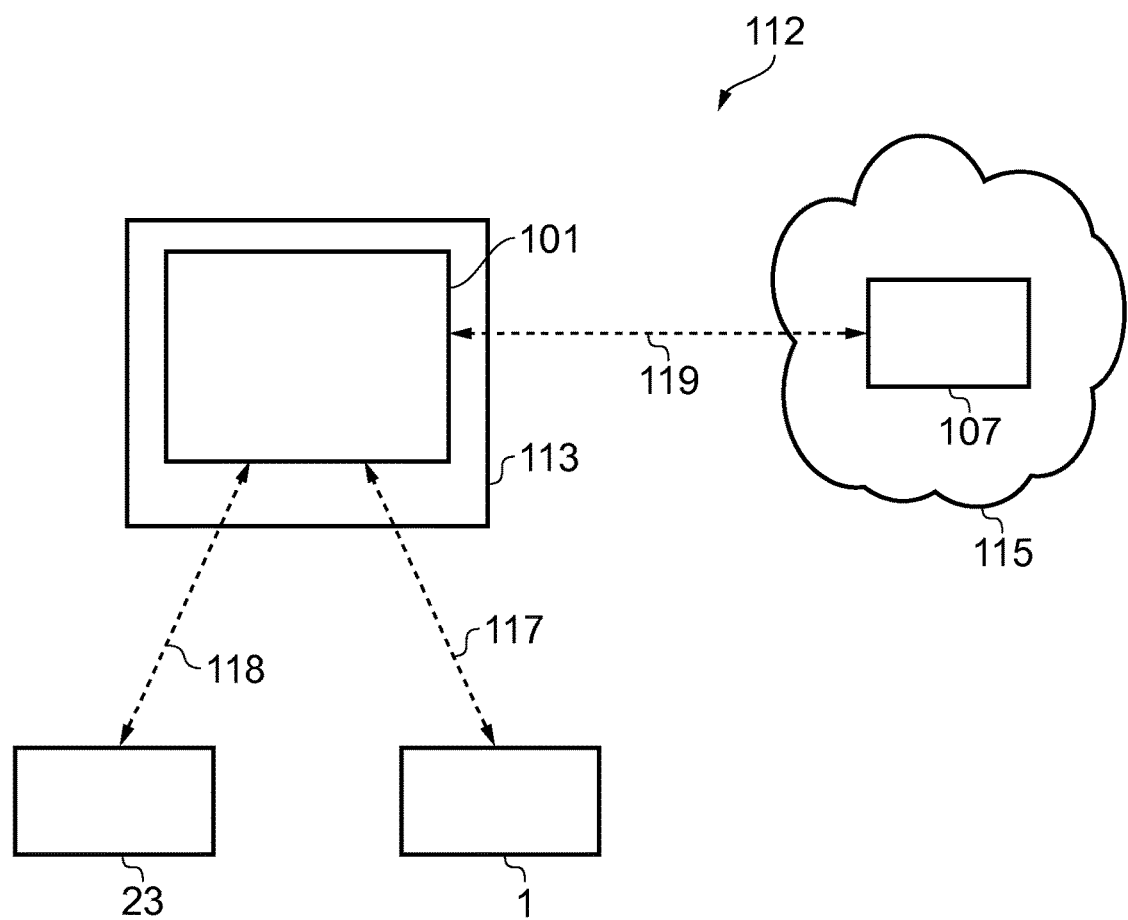

For a better understanding of various examples that are useful for understanding the detailed description, reference will now be made by way of example only to the accompanying drawings in which:

FIG. 1 illustrates an apparatus;
FIG. 2 illustrates a system comprising an apparatus;
FIG. 3 illustrates another example apparatus;
FIG. 4 illustrates a system comprising an apparatus;
FIG. 5 illustrates an example flexible x-ray detector;
FIG. 6 illustrates an example system comprising an apparatus and a plurality of x-ray sources;
FIG. 7 illustrates an example system comprising an apparatus and a plurality of x-ray sources;
FIG. 8 illustrates another example system;
FIG. 9 illustrates a method;
FIG. 10 illustrates a control apparatus; and
FIG. 11 illustrates a system comprising a control apparatus.

DETAILED DESCRIPTION

The Figures illustrate an apparatus 1 comprising: a detector 3 configured to detect electromagnetic radiation where the detector 3 comprises a first portion 9 and a second portion 11; a deformable substrate 5 configured to support the detector 3 such that the first portion 9 of detector 3 is moveable relative to the second portion 11 of the detector 3; and a sensor 7 configured to detect deformation of the substrate 5 and provide information indicative of the detected deformation to image processing circuitry 106.

The apparatus 1 may be for detecting x-rays or other electromagnetic radiation. The apparatus 1 may be for obtaining images of objects. Where the detector 3 is configured to detect x-rays the apparatus 1 may be for obtaining x-ray images of objects positioned between the apparatus 1 and an x-ray source 23.

FIG. 1 schematically illustrates an apparatus 1 according to examples of the disclosure. The example apparatus 1 comprises a detector 3, a substrate 5 and a sensor 7.

The detector 3 may comprise any means which be configured to detect electromagnetic radiation and convert the detected electromagnetic radiation into an electrical output signal.

The electromagnetic radiation detector 3 may be configured to detect x-rays and convert the detected x-rays into an electrical output signal. The x-ray detector 3 may enable an image to be obtained of an object positioned between the x-ray detector 3 and an x-ray source 23.

The x-ray detector 3 may comprise any suitable transducing material which may be configured to convert incident x-rays into an output electrical signal. In some examples the detector 3 may comprises a scintillator material which may be configured to convert incident x-rays into photons. In such examples a photodetector may be coupled to the scintillator to convert the photons into an electrical output image signal. In some examples the detector 3 may comprise a direct conversion detector which may be configured to transduce incident x-rays directly into an electrical signal. In such examples the detector 3 may comprise amorphous selenium or any other suitable material.

In some examples the detector 3 may be rigid. In such examples the detector 3 may comprise a rigid transducing material. For instance the scintillator could comprise thallium doped caesium iodide (CsI:Tl) which could be coupled to any suitable photodetector. It is to be appreciated that any suitable materials could be used in such examples.

In other examples the detector 3 may be flexible. In such examples the detector 3 may comprise a flexible material transducing material. For instance a photodetector comprising graphene could be coupled to flexible scintillator material. It is to be appreciated that any suitable flexible materials could be used in such examples.

The material that is used as the detector 3 may depend on the type of electromagnetic radiation that is to be detected by the detector 3. For instance in some examples the detector 3 may be configured to detect electromagnetic radiation from the infrared or visible region of the spectrum. In such examples the detector 3 may comprise a different material to the examples in which the detector 3 is configured to detect x-rays.

The detector 3 comprises a plurality of portions. In the example of FIG. 1 the detector 3 comprises a first portion 9 and a second portion 11. It is to be appreciated that in other examples of the disclosure the detector 3 may comprise more than two portions.

In the example of FIG. 1 the portions 9, 11 of the detector 3 are provided as separate portions so that the detector 3 comprises a plurality of individual portions. In some examples a gap may be provided between portions 9, 11 of the detector 3. In some examples the portions 9, 11 of the detector 3 may be arranged so that adjacent portions 9, 11 are touching and there is no gap between adjacent portions 9, 11. In other examples the respective portions 9, 11 of the detector 3 may be provided as contiguous portions of a single segment.

The detector 3 is provided on a deformable substrate 5. The deformable substrate 5 may comprise means for supporting the detector 3.

The deformable substrate 5 may be configured such that different portions 9, 11 of the detector 3 can be moved relative to each other. In the example of apparatus 1 of FIG. 1 the deformable substrate 5 is configured so that the first portion 9 of the detector 3 is moveable relative to the second portion 11 of the detector 3. The deformable substrate 5 may be configured to enable the deformable substrate 5 to be deformed so that the shape of the deformable substrate 5 corresponds to the shape of an object that is to be imaged by the apparatus 1.

The deformable substrate 5 may be configured to be bent or folded by the user of the apparatus 1. In some examples controlling circuitry 103 may also be configured to control the deformation of the deformable substrate 5 so that the relative positions of the portions 9, 11 of the detector 3 can be adjusted automatically without any direct input from a user of the apparatus 1.

In some examples the deformable substrate 5 may comprise a flexible material. The flexible material may comprise a flexible polymer or any other suitable material. In some examples controlling circuitry 103 may be configured to control the shape of the deformable substrate 5 by providing an electrical signal to the deformable material to cause a change in shape of the deformable material. In such examples the deformable material may comprise an electroactive polymer or any other suitable material. An example of an apparatus 1 comprising a deformable substrate which may comprise deformable material is illustrated in FIG. 4.

In some examples the deformable substrate 5 may comprise a plurality of hinged or jointed segments. The hinged or jointed segments may be rigid. The hinged or jointed segments may be configured to be moved with respect to each other to enable a portion of the deformable substrate 5 to be folded or bent. The deformable substrate 5 may be folded or bent in response to a force applied by the user of the apparatus 1 or an electrical signal provided by the controlling circuitry 103. An example of an apparatus 1 comprising a plurality of hinged segments is illustrated in FIGS. 2 and 3.

The apparatus 1 also comprises a sensor 7. The sensor 7 may be positioned within the deformable substrate 5. The sensor 7 may comprise any means which may be configured to detect deformation of the deformable substrate 5.

In some examples the sensor 7 may comprise one or more strain gauges. The strain gauges could comprise a Wheatstone bridge arrangement or any other suitable type of strain gauge.

The sensor 7 may be configured to provide an output signal comprising information indicative of the deformation of the deformable substrate 5. The sensor 7 may be configured so that the output signal may be provided to image processing circuitry 106. This enables the information indicative of the detected deformation to be used to process the image signal obtained by the detector 3.

In the example of FIG. 1 only one sensor 7 is illustrated. It is to be appreciated that in other examples a plurality of sensors 7 may be provided. The plurality of sensors 7 may be positioned at different positions within the deformable substrate 5. The plurality of sensors 7 could comprise different types of sensors 7.

It is to be appreciated that the apparatus 1 may comprise other components. For instance, in some examples the apparatus 1 may comprise one or more transmitters and/or receivers which may be configured to enable exchange of information between the apparatus 1 and remote control circuitry 103. The remote control circuitry 103 may be configured to use the image signal obtained from the detector 3 and the information indicative of the deformed deformation to process the image obtained by the detector 3. In some examples the apparatus 1 may comprise processing circuitry 103 which may be configured to process the image signals provided by the detector 3.

FIG. 2 illustrates a system 21 according to examples of the disclosure. The system 21 comprises an apparatus 1 and an x-ray source 23.

The apparatus 1 may comprise a detector 3, a deformable substrate 5 and a sensor 7 as described above. Corresponding reference numerals are used for corresponding features.

In the example of FIG. 2 the deformable substrate 5 comprises a plurality of hinged segments. In the example of FIG. 2 the deformable substrate comprises a first hinged segment 25 and a second hinged segment 26. A hinge 27 is provided between the two hinged segments 25, 26 and configured to enable the hinged segments 25, 26 to be moved relative to each other.

In some examples the segments 25, 26 of the deformable substrate 5 may be rigid so that the deformable substrate 5 only deforms at the hinge 27. In such examples the segments 25, 26 might not deform. In other examples the segments 25, 26 of the deformable substrate 5 could be deformable so that the deformable substrate 5 could deform at portions other than the hinge 27.

In the example of FIG. 2 each of the segments 25, 26 of the deformable substrate 5 comprises a flat or substantially flat surface. The flat surfaces are configured to support the portions 9, 11 of the detector 3. In other examples the segments 25, 26 of the deformable substrate 5 might have other shapes. For example, the segments could be curved. The size and shape of the segments 25, 26 of the deformable substrate 5 might depend on the objects that the system 21 is intended to image.

In the example of FIG. 2 the first portion 9 of the detector 3 is provided on the first segment 25 of the deformable substrate 5 and the second portion 11 of the detector 3 is provided on the second segment 26 of the deformable substrate 5. As the hinge 27 enables the hinged segments 25, 26 to be moved relative to each other this enables the portions 9, 11 of the detector 3 to be moved relative to each other.

The portions 9, 11 of the detector 3 may be provided on the segments 25, 26 of the deformable substrate 5 so that the first portion 9 of the detector 3 covers all of or substantially all of a first surface of the first segment 25. Similarly the second portion 11 of the detector 3 may cover all of or substantially all of the first surface of the second segment 26 of the deformable substrate 5.

The material that is used for detecting x-rays within the detector 3 may depend on whether the segments 25, 26 of the deformable substrate 5 are rigid or flexible. If the segments 25, 26 of the deformable substrate 5 are rigid then the detector 3 may also comprise rigid materials. If the segments 25, 26 of the deformable substrate 5 are deformable then the detector 3 may comprise a flexible detector.

The example apparatus 1 of FIG. 2 comprises a sensor 7 positioned within the hinge 27. The sensor 7 may be configured to detect movement of the hinge 27. In the example of FIG. 2 the sensor 7 may be able to detect the angle θ between the two segments 25, 26 of the deformable substrate 5 and provide an output indicative of the angle θ. This information obtained by the sensor 7 may be used by image processing circuitry 106 to correct an image obtained by the detector 3.

In the example of FIG. 2 the system 21 also comprises an x-ray source 23. The source of x-ray source 23 may be positioned relative to the apparatus 1 so that x-rays emitted by the x-ray source 23 are incident on the detector 3. This enables an image of an object positioned between the x-ray source 23 and the apparatus 1 to be obtained by the detector 3.

The x-ray source 23 may comprise any means which may be configured to generate x-rays.

When the system 21 is in use an object which is to be imaged is positioned between the x-ray source 23 and the apparatus 1. The deformable substrate 5 is deformed so that the shape of the deformable substrate 5 corresponds to the shape of the object that is to be imaged. The deformable substrate 5 may be adjusted to fit to the object that is to be imaged so that the distance between the object and the detector 3 is consistent across the surface of the object.

In the example apparatus of FIG. 2 both of the segments 25, 26 of the deformable substrate 5 are flat. In other examples the hinged segments 25, 26 could have different shapes. In some examples the different segments 25, 26 could have different radius of curvature.

In the example of FIG. 2 the detector 3 is configured to detect x-rays and so the system comprises an x-ray source 23. The x-ray source 23 is provided separate to the apparatus 1 so that the object to be imaged can be positioned between the apparatus 1 and the x-ray source.

In other examples where the detector 3 is configured to detect electromagnetic radiation within a different range of the electromagnetic spectrum the electromagnetic radiation source could be provide within the apparatus 1. For instance, if the apparatus 1 is arranged to detect infrared radiation or visible light these wavelengths might not penetrate through the object that is to be imaged. For example, if the apparatus 1 is being used to image a person or animal the penetration of visible light or infrared radiation through the tissues of the person or animal might be insufficient to enable images to be obtained. In such examples the electromagnetic radiation source could be mounted on the deformable substrate or in any other suitable position.

The electromagnetic radiation source within the apparatus 1 may be controlled so that the exposure of the electromagnetic radiation can be optimized. For instance the electromagnetic radiation source within the apparatus 1 may be configured to obtain information from the one or more sensors indicative of the deformations of the deformable substrate 5. This information may be used to control the parameters of the electromagnetic radiation source such as intensity, direction or other parameter. In some examples information obtained from the detector 3 may be used to determine the intensity of electromagnetic radiation that is being detected. This may enable the electromagnetic radiation exposure to be optimized. This may provide a more efficient apparatus 1 and may reduce the dosage of electromagnetic radiation needed to obtain an image. FIG. 3 schematically illustrates another example apparatus 1 where different segments of a deformable substrate 5 have different shapes. The apparatus 1 comprises a detector 3, a deformable substrate 5 and a plurality of sensors 7.

In the example of FIG. 3 the deformable substrate 5 comprises a plurality of hinged segments 31, 33, 34 which may be arranged to move relative to each other as described above. In the example of FIG. 3 the deformable substrate 5 comprises three segments 31, 33, 34. The three segments 31, 33, 34 comprise a curved segment 31 which is provided in the centre of the apparatus 1 and a first flat segment 33 provided on a first side of the curved segment 31 and a second flat segment 34 provided on the other side of the curved segment 33. The flat segments 33, 34 have a different radius of curvature to the curved segment 31.

A plurality of hinges 35, 36 are provided within the deformable substrate 5 to enable the segments 31, 33, 34 to be moved relative to each other. In the example of FIG. 3 two hinges 35, 36 are provided. A first hinge 35 is provided between the curved segment 31 and the first flat segment 33 and a second hinge 36 is provided between the curved segment 31 and the second flat segment 34.

In the example of FIG. 3 the detector 3 also comprises a plurality of portions 37, 39, 40. A first portion 37 is provided on the curved segment 31. The first portion 37 of the detector 3 may be curved. The second portion 39 of the detector 3 is provided on the first flat segment 33 and the third portion 40 is provided on the second flat segment 34. As the hinges 35, 36 enable the segments 31, 33, 34 of the deformable substrate 5 to be moved relative to each other this enables the portions 37, 39, 40 of the detector 3 to be moved relative to each other.

The apparatus 1 also comprises a plurality of sensors 7. In the example of FIG. 3 the sensors 7 are positioned within each of the hinges 35, 36 so that the sensors 7 can detect information indicative of the relative positions of the segments 31, 33, 34 of the deformable substrate 5. This information may be used by image processing circuitry 106 to correct an image obtained by the detector 3.

The apparatus 1 of FIG. 3 may be suitable for use in an intraoral device for obtaining images of a user's teeth. In use the apparatus 1 may be positioned within the patient's mouth. The first curved segment 31 may be positioned adjacent to the patient's front teeth and the side segments 33, 34 may be positioned adjacent to the patient's side teeth. The hinges 35, 36 enable the apparatus 1 to be adjusted to fit to the teeth of the patient. This may enable the same apparatus 1 to be used to fit to different patients. It is to be appreciated that different sized and shaped apparatus 1 may be used to enable different types of objects to be imaged.

FIG. 4 illustrates another example system 41 according to examples of the disclosure. The system 41 also comprises an apparatus 1 and an x-ray source 23 which may be as described above. The apparatus 1 comprises a detector 3, a deformable substrate 5 and a sensor 7 as described above. Corresponding reference numerals are used for corresponding features.

In the example of FIG. 4 the deformable substrate 5 comprises a flexible material. The flexible material may comprise any material or combination of materials which is strong enough to support the detector 3 but flexible enough to be bent or otherwise deformed by a user of the apparatus 1.

In the example of FIG. 4 the deformable substrate 5 has been deformed into a curved shape. The deformable substrate 5 may be deformed into any suitable shape depending on the object that is to be imaged.

In the example of FIG. 4 the detector 3 is provided on a surface of the deformable substrate 5. The detector 3 may be configured to cover all or substantially all of the surface of the deformable substrate 5. This may provide a large surface area for detecting x-rays.

The detector 3 comprises a plurality of different portions 43, 44. In the example of FIG. 4 the detector 3 comprises a single segment so that the different portions 43, 44 of the detector 3 are provided as contiguous portions of the same segment. The detector 3 may be a flexible detector so that the detector 3 is deformed when the deformable substrate 5 is deformed. This enables the respective portions 43, 44 of the detector 3 to be moved relative to each other.

The deformable substrate 5 also comprises one or more sensors 7. The one or more sensors 7 may be configured to detect the bending or other deformation of the deformable substrate 5. In the example of FIG. 4 the sensors 7 are provided embedded within the deformable substrate 5. In other examples the sensors 7 may be positioned in any suitable location within the apparatus 1.

In the example system of FIG. 4 the sensors 7 may be configured to provide information indicative of the radius of curvature r. This information may be used by image processing circuitry 106 to correct an image obtained by the detector 3.

The sensors 7 may also be configured to detect deformation of the detector 3. Where the detector 3 is a flexible detector the detector 5 may also be bent or stretched or otherwise deformed as the deformable substrate 5 is deformed. Information about the deformation of the detector may be used by the image processing circuitry to correct the obtained images.

FIG. 5 schematically illustrates an example of a flexible detector 3 that may be used to detect x-rays in some examples of the disclosure. The flexible detector 3 may be provided on a deformable substrate 5 as described above.

In the example of FIG. 5 the flexible detector 3 may comprise a scintillator 51 and a photodetector 53. The scintillator 51 may be configured to convert x-rays incident on the detector 3 into photons and guide the photons towards the photodetector 53. The photons generated by the scintillator 51 may be incident upon the photodetector 53. The photodetector 53 may comprise any means which may be configured to convert the incident photons into an electrical output image signal. The image signal may be provided to image processing circuitry 106 to enable an image indicative of the incident x-rays to be rendered.

The scintillator 51 and the photodetector 53 may comprise any suitable flexible materials. In some examples the photodetector 53, or any other suitable part of the detector 3, may comprise graphene or any other suitable flexible material.

FIG. 6 illustrates another system 61 according to examples of the disclosure. The system 61 also comprises and apparatus 1 and an x-ray source 23. The apparatus 1 in the example system of FIG. 6 may be the same as the apparatus 1 illustrated in FIG. 2. Corresponding reference numerals are used for corresponding features.

In the example system 61 of FIG. 6 the x-ray source 23 may be configured to be moved between a first position 63 and a second position 64. The different positions 63, 64 may enable the x-ray source 23 to be configured to emit x-rays in different directions.

The system 61 of FIG. 6 may be arranged so that when the x-ray source 23 is positioned in the first position 63 x-rays emitted by the x-ray source 23 are incident on the first portion 9 of the detector 3 and when the x-ray source 23 is positioned in the second position 64 x-rays emitted by the x-ray source 23 are incident on the second portion 11 of the detector 3.

In the example of FIG. 6 when the x-ray source 23 is in the first position 63 the x-ray rays are emitted perpendicular or substantially perpendicular to the first portion 9 of the detector 3. When the x-ray source 23 is in the second position 64 the x-rays are emitted perpendicular of substantially perpendicular to the second portion 11 of the detector 3. This may increase the absorption of x-rays by the apparatus 1.

The portions 9, 11 of the detector 3 may obtain a plurality of images which may then be combined into a single image by the image processing circuitry 106.

FIG. 7 illustrates another system 71 according to examples of the disclosure. The system 71 also comprises an apparatus 1 and an x-ray source 23. The apparatus 1 in the example system of FIG. 7 may be the same as the apparatus 1 illustrated in FIG. 4. Corresponding reference numerals are used for corresponding features.

In the example system 71 of FIG. 7 the x-ray source 23 may be configured to be moved between a first position 73 and a second position 74. As in the example of FIG. 6 the different positions 73, 74 may enable the x-ray source 23 to be configured to emit x-rays in different directions.

The system 71 of FIG. 7 may be arranged so that when the x-ray source 23 is positioned in the first position 73 x-rays emitted by the x-ray source 23 are incident on the first portion 43 of the detector 3 and when the x-ray source 23 is positioned in the second position 74 x-rays emitted by the x-ray source 23 are incident on the second portion 44 of the detector 3.

In the example of FIG. 7 when the x-ray source 23 is in the first position 73 the x-ray rays are emitted perpendicular or substantially perpendicular to the first portion 43 of the detector 3. When the x-ray source 23 is in the second position 74 the x-rays are emitted perpendicular of substantially perpendicular to the second portion 44 of the detector 3. This may increase the absorption of x-rays by the apparatus 1.

The portions 43, 44 of the detector 3 may obtain a plurality of images which may then be combined into a single image by the image processing circuitry 106.

In the example of FIGS. 6 and 7 the x-ray source 23 may be positioned in two different positions 63, 64, 73, 74. It is to be appreciated that in other examples of the disclosure the x-ray source 23 may be positioned in any number of different positions.

In the examples of FIGS. 6 and 7 the systems 61, 71 may comprise control circuitry 103 which may be configured to control the positions of the x-ray source 23. In such examples the control circuitry 103 may obtain information from one or more sensors 7 indicative of the deformation of the deformable substrate 5 to enable the x-ray source 23 to be aligned with the positions of the respective portions 9, 11, 43, 44 of the detector 3.

In some examples different exposure settings may be used by the x-ray source 23 in the different positions. This may enable information to be obtained from a first portion of the detector 3 with first exposure settings and the information to be obtained from a second portion of the detector 3 with second exposure settings where the first exposure settings and the second exposure settings are different. This may enable optimal settings to be used to obtain images from different portions of the detector 3. In some examples information indicative of the deformation of the deformable substrate 5 may be used to control the exposure settings. For instance information indicative of the deformation of the deformable substrate 5 may be used to determine the position of the detector 3 relative to the x-ray source 23 and may enable the optimal exposure settings for the current arrangement of the system 61, 71 to be determined. Information relating to the optimal exposure settings may then be used to control the x-ray source 23.

In the examples of FIGS. 6 and 7 the systems 61, 71 comprise a single x-ray source 23 that is moved between different positions 63, 64, 73, 74. In other examples the systems 61, 71 could comprise a plurality of different x-ray sources 23. The different x-ray sources 23 may provide x-rays to be incident on different portions of the detector 3. This may enable images to be obtained simultaneously from the different portions of the detector 3.

As described above, in some examples the apparatus 1 may comprise a source of electromagnetic radiation mounted on the deformable substrate 5 or in any other suitable position. In such examples a plurality of different electromagnetic radiation sources 5 may be provided at different positions on the deformable substrate 5 to enable images to be obtained from the different portions of the detector 3.

In some examples information obtained from the detector 3 may be used to control the exposure settings of the x-ray source 23 or the source of other electromagnetic radiation. For instance information indicative of the intensity of x-rays or other electromagnetic radiation may be obtained by the detector 3 and provided to control circuitry 103. The control circuitry 103 may used the information regarding the detected x-rays or other radiation to optimize the positions, intensity or other parameters of the x-ray source 23 or source of electromagnetic radiation. This may enable information obtained from the detector 3 to control exposure settings of the various electromagnetic radiation sources.

FIG. 8 illustrates another example system and images that may be obtained using the example system. In FIG. 8 the system that is used is the same as the system of FIG. 4. Corresponding reference numerals may be used for corresponding features. It is to be appreciated that any other suitable systems may be used in other examples of the disclosure.

In the example of FIG. 8 the apparatus 1 is being used to image a patient's teeth 81. The deformable substrate 5 is deformed so that the apparatus 1 fits closely to the patient's teeth 81. The apparatus 1 is sized and shaped to fit into the patient's mouth so that, in use, the patient's teeth 81 are positioned between the x-ray source 23 and the apparatus 1.

The apparatus 1 may be used to obtain images 83, 85, 87, 89 of the teeth 81. FIG. 8 illustrates example images 83, 85, 87, 89 that may be obtained in various examples of the disclosure.

The first image 83 is a flat two dimensional image. The image may be corrected using any suitable technique or algorithm to project the curved structure of the teeth 81 onto a flat plane. Information indicative of the deformation of the substrate 5 may be used to project the image onto the planar surface. The flat may be useful in that they may be viewed on a two dimensional surface, for instance, they may be printed onto paper or other formats.

The other images 85, 87, 89 are curved images in which image information obtained by the detector 3 is projected onto a curved plane. The curvature of the plane may be determined by the curvature of the apparatus 1. Information indicative of the curvature of the deformable substrate 5 may be obtained from sensors within the deformable substrate to determine the curvature of the plane that is to be used. The curvature of the plane that is used for the image may match the curvature of the apparatus 1 so that a user may obtain spatial information of the user's teeth 81 by viewing the curved images.

In the second example image 85 the curved surface has a first radius of curvature. In the third example image 87 the curved surface has a second radius of curvature. The second radius of curvature is larger than the first radius of curvature so that the third example image 87 is less curved than the second example image 85. In the fourth example image 89 the curved surface has a third radius of curvature. The third radius of curvature is smaller than the first radius of curvature so that the fourth example image 89 is more curved than the second example image 85. It is to be appreciated that other radius of curvature may be used in other examples of the disclosure.

In some examples the system 41 may comprise a user interface a controlling circuitry 103 configured to enable the images 83, 85, 87, 89 to be displayed on the user interface. The user interface may enable the images 83, 85, 87, 89 so that a user can view the curved images from different perspectives. This may enable more accurate information about the patient's teeth 81 to be obtained from the image as it reduces distortions made when the image is projected onto a flat plane.

FIG. 9 illustrates a method that may be implemented using apparatus 1 and systems as described above. At block 91 the method comprises obtaining an image signal from a detector 3 for detecting x-rays where the detector 3 comprises a first portion and a second portion and is supported on a deformable substrate 5 such that deformation of the deformable substrate enables the first portion to be moved relative to the second portion. At block 93 the method comprises obtaining a deformation signal from the deformable substrate 5 comprising information indicative of the deformation of the substrate 5. At block 95 the method comprises using the information indicative of the deformation to process the image signal.

In some examples the method may comprise additional blocks. For instance, where the x-ray source 23 is moved between a plurality of different positions a plurality of image signals may be obtained. The information indicative of the deformation of the substrate 5 may be used to enable the different image signals to be combined to render a single combined image. The use of the information indicative of the deformation of the substrate 5 may enable the images to be combined so that discontinuations and artifacts within the image are reduced.

FIG. 10 illustrates a control apparatus 101. The control apparatus 101 may be used to control the example apparatus 1 and systems described above. The control apparatus 101 may be used to implement the methods as described above.

The control apparatus 101 illustrated in FIG. 10 may be a chip or a chip-set. In some examples the control apparatus 101 may be provided within an apparatus 1 or system 21, 41, 61, 71 as described above. The control apparatus 101 may be provided separate to the apparatus 1 but may be arranged to enable information to be exchanged between the control apparatus 101 and the apparatus 1.

The example control apparatus 101 comprises controlling circuitry 103. The controlling circuitry 103 may provide means for controlling an apparatus 1 and/or system as describe above. For instance, the controlling circuitry 103 may provide means for controlling the deformation of the deformable substrate 5. For instance where the apparatus 1 is used in intraoral devices the apparatus may be positioned within the user's mouth. When the apparatus 1 is positioned within the user's mouth it may be difficult to adjust the shape of the apparatus 1 manually. In such cases the apparatus 1 may be configured to receive a signal from the control apparatus 101 to control the deformation of the deformable substrate 5. This may enable the apparatus 1 to be easily adjusted for different patients.

In some examples the controlling circuitry 103 may provide means for controlling the exposure settings of one or more x-ray sources 23 and/or means for controlling the positions of one or more x-ray sources 23. For instance, in the systems of FIGS. 6 and 7 as described above different x-ray sources 23 and settings may be used. In such systems the controlling circuitry 103 may obtain information indicative of the deformation of the apparatus 1 and use that information to determine the best positions for the x-rays sources 23 and/or the best exposure settings for the x-ray sources 23. The controlling circuitry 103 may be configured to provide a control signal to control the x-ray sources 23.

The controlling circuitry 103 may also provide means for performing the methods or at least part of the methods of examples of the disclosure.

The processing circuitry 105 may be configured to read from and write to memory circuitry 107. The processing circuitry 105 may comprise one or more processors. The processing circuitry 105 may also comprise an output interface via which data and/or commands are output by the processing circuitry 105 and an input interface via which data and/or commands are input to the processing circuitry 105.

In some examples the processing circuitry 105 may comprise image processing circuitry 106. The image processing circuitry 106 may comprise any means which may be configured to receive an image signal from the detector 3 and convert the received image signal into an image output. The image output may be displayed on a display or other user interface. The image processing circuitry 106 may be configured to process the image signal before the image output is provided. The image processing circuitry 106 may be configured to use information indicative of the deformation of the substrate 5 obtained from the sensor 7 to process the received image signal and correct the image output.

The memory circuitry 107 may be configured to store a computer program 109 comprising computer program instructions (computer program code 111) that controls the operation of the control apparatus 101 when loaded into processing circuitry 105. The computer program instructions, of the computer program 109, provide the logic and routines that enable the control apparatus 101 to perform the example methods illustrated in FIG. 9. The processing circuitry 105 by reading the memory circuitry 107 is able to load and execute the computer program 109.

The control apparatus 101 therefore comprises: processing circuitry 105; and memory circuitry 107 including computer program code 111, the memory circuitry 107 and the computer program code 111 configured to, with the processing circuitry 105, cause the control apparatus 101 at least to perform: obtaining an image signal from a detector 3 for detecting x-rays where the detector 3 comprises a first portion 9 and a second portion 11 and is supported on a deformable substrate 5 such that deformation of the substrate 5 enables the first portion 9 to be moved relative to the second portion 11; obtaining a deformation signal from the deformable substrate 5 comprising information indicative of the deformation of the substrate 5; and using the information indicative of the deformation to process the image signal.

The computer program 109 may arrive at the control apparatus 101 via any suitable delivery mechanism. The delivery mechanism may be, for example, a non-transitory computer-readable storage medium, a computer program product, a memory device, a record medium such as a compact disc read-only memory (CD-ROM) or digital versatile disc (DVD), or an article of manufacture that tangibly embodies the computer program. The delivery mechanism may be a signal configured to reliably transfer the computer program 109. The apparatus may propagate or transmit the computer program 109 as a computer data signal. In some examples the computer program code 111 may be transmitted to the apparatus 1 using a wireless protocol such as Bluetooth, Bluetooth Low Energy, Bluetooth Smart, 6LoW-Pan (IP$_v$6 over low power personal area networks) ZigBee, ANT+, near field communication (NFC), Radio frequency identification, wireless local area network (wireless LAN) or any other suitable protocol.

Although the memory circuitry 107 is illustrated as a single component in the figures it is to be appreciated that it may be implemented as one or more separate components some or all of which may be integrated/removable and/or may provide permanent/semi-permanent/dynamic/cached storage.

In the example of FIG. 10 the memory circuitry 107 is illustrates within the control apparatus 101. In some examples one or more components of the memory circuitry 107 could be located remote to the control apparatus 101. For instance, one or more components of the memory circuitry 107 could be located on a remote device, such as a remote server, which is accessible by the control apparatus 101. This may enable cloud storage of information such as x-ray images obtained by the apparatus 1.

Although the processing circuitry 105 is illustrated as a single component in the figures it is to be appreciated that it may be implemented as one or more separate components some or all of which may be integrated/removable.

References to "computer-readable storage medium", "computer program product", "tangibly embodied computer program" etc. or a "controller", "computer", "processor" etc. should be understood to encompass not only computers having different architectures such as single/multi-processor architectures, Reduced Instruction Set Computing (RISC) and sequential (Von Neumann)/parallel architectures but also specialized circuits such as field-programmable gate arrays (FPGA), application-specific integrated circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term "circuitry" refers to all of the following:
(a) hardware-only circuit implementations (such as implementations in only analog and/or digital circuitry) and
(b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and
(c) to circuits, such as a microprocessor(s) or a portion of a microprocessor(s), that require software or firmware for operation, even if the software or firmware is not physically present.

This definition of "circuitry" applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

FIG. 11 illustrates an example system 112 comprising a control apparatus 101. The system 112 comprises an apparatus 1, at least one x-ray source 23 a control apparatus 101 and a remote device 115.

The control apparatus 101 may be as described in relation to FIG. 10. The control apparatus may be provided within an electronic device 113. The electronic device 113 could be a communications device such as a tablet or mobile phone or any other suitable device.

The electronic device 113 may comprise a display. In some examples the display could be contained within the electronic device 113. In some examples the display may be a peripheral device which the control apparatus 101 can communicate with. The control apparatus 101 may be configured to control the display to display images obtained from the apparatus 1.

The control apparatus 101 may enable a communication link 117 to be established between the apparatus 1 and the electronic device 113. The communication link 117 may be a wireless communication link. The communication link 117 may be a short range wireless communication link.

The communication link 117 may enable control signals to be provided from the control apparatus 101 to the apparatus 1. The control signals may be used to control the deformation of the deformable substrate 5 of the apparatus, to obtain information from the apparatus 1 or to control the apparatus 1 to perform any other suitable function.

The communication link 117 may also enable information obtained by the apparatus 1 to be provided to the control apparatus 101. The information may comprise image information obtained by the detector 3 of the apparatus 1, deformation information obtained by a sensor 7 of the apparatus 1 or any other suitable information. This information may be used to enable the control apparatus 101 to perform methods as described above.

The control apparatus 101 may also enable a communication link 118 to be established between the one or more x-ray sources 23 and the electronic device 113. The communication link 118 may be a wireless communication link. The communication link 118 may be a short range wireless communication link.

The communication link 118 may enable control signals to be provided from the control apparatus 101 to the x-ray sources 23. The control signals may be used to control the positions of the x-ray sources 23, the exposure settings of the x-ray sources 23 or any other suitable functions or settings of the x-ray sources 23.

The remote device 115 may comprise memory circuitry 107. The remote device may comprise a server or any other suitable type of device which may enable information to be stored remotely. The remote device 115 may enable cloud storage of information obtained by the control apparatus 101. The remote device 115 may enable cloud storage of images obtained by the apparatus 1.

The control apparatus 101 may enable a communication link 119 to be established between the remote device 115 and the electronic device 113. The communication link 119 may be a wired or a wireless communication link. The communication link 119 may be a short range wireless communication link or a long range wireless communication link.

The communication link 119 may enable information to be exchanged between the electronic device 113 and the remote device 115. The information that is exchanged could comprise information obtained from an apparatus 1 as described above. For instance the communication link 119 may enable image information to be transmitted to the remote device 115. This may enable information such as images obtained by the apparatus 1 to be stored at the remote device 115 and retrieved from the remote device 115 when needed.

Examples of the disclosure provide a deformable x-ray detector apparatus 1. Information indicative of the deformation of the apparatus 1 may be used to correct image information obtained by the apparatus 1 to enable high quality x-ray images to be rendered.

As the x-ray detector 3 can be deformed into any suitable shape this may enable the shape of the detector 3 to closely follow the shape of the object that is to be images. This may enable a consistent separation to be provided between the object and the detector 3. This may provide an improved image quality and reduce the x-ray exposure needed. This may also enable the whole of the object to be imaged at once and may reduce the total number of images and so reduce the overall exposure to x-rays.

Using a deformable x-ray detector 3 provides the advantage that it may make it easier to insert the x-ray detector 3 into position. For instance, the x-ray detector apparatus may be folded to have a smaller cross section to fit into a cavity and then may be unfolded once it is within the cavity to enable high quality images of objects within the cavity to be obtained.

Having a deformable x-ray detector 3 enables the same apparatus to be used to image different objects. For instance, where the apparatus 1 is used in an intraoral x-ray device the same apparatus 1 can be adjusted to use with patients having different sized mouths. This means that the dentist does not need to have multiple different sized and shaped x-ray detectors 3. Also in such implementations the deformable x-ray device may be more comfortable for the patient. If the deformable substrate 5 is a flexible substrate the apparatus 1 would not comprise any sharp or rigid edges or corners which could be uncomfortable for the patient.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
    a detector configured to detect electromagnetic radiation, wherein the detector comprises at lea a first portion and a second portion, wherein the first portion and the second portion are configured to obtain images of different objects;
    a deformable substrate configured to support the detector, wherein the first portion of detector is turnable relative to the second portion of the detector; and
    a sensor configured to detect deformation of the substrate, said deformation being an amount by which the first portion is turned relative to the second portion, said sensor being further configured to provide information indicative of the detected deformation to image processing circuitry, wherein said information indicative of the detected deformation is configured to correct an image obtained by said apparatus for projection of the image onto flat or curved surfaces.

2. The apparatus according to claim 1, wherein the detector for detecting electromagnetic radiation comprises a flexible detector.

3. The apparatus according to claim 2, wherein the flexible detector comprises graphene.

4. The apparatus according to claim 1, wherein the deformable substrate comprises a flexible substrate.

5. The apparatus according to claim 1, wherein the deformable substrate comprises a plurality of hinged segments.

6. The apparatus according to claim 5, wherein the plurality of hinged segments comprises at least one segment having a first radius of curvature and at least one segment comprising a second radius of curvature where the first radius of curvature and the second radius of curvature are different.

7. The apparatus according to claim 1, further comprising a controller configured to control the deformation of the substrate.

8. The apparatus according to claim 1, wherein the electromagnetic radiation detector comprises an intraoral electromagnetic radiation detector.

9. A system comprising an apparatus comprising:
    a detector configured to detect electromagnetic radiation, wherein the detector comprises at least first portion and a second portion, wherein the first portion and the second portion are configured to obtain images of different objects;
    a deformable substrate configured to support the detector, wherein the first portion of detector is turnable relative to the second portion of the detector;
    a sensor configured to detect deformation of the substrate, said deformation being an amount by which the first portion is turned relative to the second portion, said sensor being further configured to provide information indicative of the detected deformation to image processing circuitry, wherein said information indicative of the detected deformation is configured to correct an image obtained by said apparatus for projection of the image onto flat or curved surfaces; and
    at least one electromagnetic radiation source.

10. The system according to claim 9, wherein the system comprises a plurality of electromagnetic radiation sources, wherein a first electromagnetic radiation source is configured to provide electromagnetic radiation to a first portion of the electromagnetic radiation detector and a second electromagnetic radiation source is configured to provide electromagnetic radiation to the second portion of the electromagnetic radiation detector.

11. The system according to claim 9, wherein the system comprises an electromagnetic radiation source configured to be moved between a first position and a second position, wherein, in the first position, the electromagnetic radiation source is configured to provide electromagnetic radiation to a first portion of the electromagnetic radiation detector and, in the second position, the electromagnetic radiation source is configured to provide electromagnetic radiation to the second portion of the electromagnetic radiation detector.

12. The system according to claim 9, wherein one or more electromagnetic radiation sources are provided on the deformable substrate.

13. A method comprising:
obtaining an image signal from a detector for detecting electromagnetic radiation, wherein the detector comprises least a first portion and a second portion and is supported on a deformable substrate, wherein deformation of the deformable substrate enables the first portion to be turned relative to the second portion, and wherein the first portion and the second portion are configured to obtain images of different objects;
obtaining a deformation signal from a sensor in the deformable substrate, the deformation signal comprising information indicative of the deformation of the substrate, said deformation being an amount by which the first portion is turned relative to the second portion; and
using the information indicative of the deformation to process the image signal, wherein said information indicative of deformation is configured to correct an image obtained by an apparatus for projection of the image onto flat or curved surfaces.

14. The method according to claim 13, wherein the image signal comprises information obtained from a first portion of the detector and information obtained from the second portion of the detector.

15. The method according to claim 13, wherein the information obtained from a first portion of the detector is obtained with first exposure settings and the information obtained from a second portion of the detector is obtained with second exposure settings, wherein the first exposure settings and the second exposure settings are different from one another.

16. The method according to claim 15, wherein the method comprises using the information indicative of the deformation of the substrate to control at least one of the first and second exposure settings.

17. The method according to claim 15, wherein the method comprises using the information from the detector to control at least one of the first and second exposure settings.

18. The method according to claim 13, wherein the method fiuher comprises controlling a first electromagnetic radiation source to provide electromagnetic radiation to a first portion of the detector and controlling a second electromagnetic radiation source to provide electromagnetic radiation to a second portion of the detector.

19. The method according to claim 13, wherein the method comprises controlling an electromagnetic radiation source to be moved between a first position for providing electromagnetic radiation to a first portion of the detector and a second position for providing electromagnetic radiation to a second portion of the detector.

20. A non-transitory computer-readable medium comprising program instructions stored thereon for performing at least the following:
obtaining an image signal from a detector for detecting electromagnetic radiation, wherein the detector comprises at least a first portion and a second portion and is supported on a deformable substrate, wherein deformation of the substrate enables the first portion to be turned relative to the second portion, and wherein the first portion and the second portion are configured to obtain images of different objects;
obtaining a deformation signal from a sensor comprised by the deformable substrate, the deformation signal comprising information indicative of the deformation of the substrate, said deformation being an amount by which the first portion is turned relative to the second portion; and
using the information indicative of the deformation to process the image signal, wherein said information indicative of deformation is configured to correct an image obtained by an apparatus for projection of the image onto flat or curved surfaces.

* * * * *

UNITED STATES PATENT AND TRADEMARK OFFICE
CERTIFICATE OF CORRECTION

PATENT NO. : 10,386,501 B2
APPLICATION NO. : 15/779149
DATED : August 20, 2019
INVENTOR(S) : Vuokko Lantz and Lea Myyrylainen Page 1 of 1

It is certified that error appears in the above-identified patent and that said Letters Patent is hereby corrected as shown below:

In the Claims

In Claim 1: Column 17, Line 64, delete "lea" and insert --least--.

In Claim 13: Column 19, Line 10, before "least" insert --at--.

In Claim 18: Column 20, Line 7, delete "fiuher" and insert --further--.

Signed and Sealed this
Fifteenth Day of October, 2019

Andrei Iancu
*Director of the United States Patent and Trademark Office*